United States Patent

Cavazza

[11] 4,021,433
[45] May 3, 1977

[54] DERIVATIVE OF NICOTINIC ACID WITH AMIDES

[75] Inventor: Claudio Cavazza, Rome, Italy

[73] Assignee: Sigma-Tau Industrie Farmaceutiche Riunite S.p.A., Italy

[22] Filed: Mar. 19, 1976

[21] Appl. No.: 668,498

Related U.S. Application Data

[63] Continuation-in-part of Ser. No. 451,694, March 15, 1974, abandoned.

[52] U.S. Cl. ................ 260/294.8 D; 260/295.5 A; 424/266
[51] Int. Cl.² .................................. C07D 213/56
[58] Field of Search ............. 260/294.8 D; 424/266

[56] References Cited

UNITED STATES PATENTS 3,155,672  11/1964  Pasini et al. ................ 260/295 AM
3,758,485  9/1973  Biniecki et al. ............. 260/295.5 A Primary Examiner—Alan L. Rotman Attorney, Agent, or Firm—Robert E. Burns; Emmanuel J. Lobato; Bruce L. Adams

[57] ABSTRACT

A novel cysteine thiolactone of nicotinamide is disclosed having the formula:

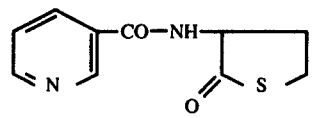

The compounds, homo-cysteine thiolactone of nicotinamide, and its pharmacologically acceptable salts have the useful pharmacological activity of lowering cholesterol, free fatty acid and triglyceride plasma level in the case of altered lipid metabolism and improving BSP clearance ratio in cases of liver injury.

A synthesis of the compound from nicotinoyl chloride, hydrochloride or nicotinic acid esters is described as well as modes for the administration of the compound.

1 Claim, 3 Drawing Figures

EFFECT OF ST$_{22}^*$ ON LIPID MOBILISATION, 156 MG/KG OS, IN 17-HOUR FASTED RATS (10 PER GROUP). PLASMA AVERAGE VALUES ± S.E.M. I PER CENT OF VALUES IN CONTROLS (F.F.A. 1119 ±69, TRIGLYCERIDES 93±9) VS HOURS AFTER ADMINISTRATION. F.F.A. (——); TRIGLYCERIDES (----). □, ■, △ AND ▲ INDICATE NON-SIGNIFICANT DIFFERENCE, P=.05, P=.01 AND P=.001 SIGNIFICANT DIFFERENCE RESPECTIVELY.

* HOMO-CYSTEINE THIOLACTONE NICOTINAMIDE

EFFECT OF $ST_{22}^*$ ON LIPID MOBILISATION, 156 MG/KG OS, IN 17-HOUR FASTED RATS (10 PER GROUP). PLASMA AVERAGE VALUES ± S.E.M. I PER CENT OF VALUES IN CONTROLS (F.F.A. 1119±69, TRIGLYCERIDES 93±9) VS HOURS AFTER ADMINISTRATION. F.F.A. (———); TRIGLYCERIDES (-----). □, ▨, △ AND ▲ INDICATE NON-SIGNIFICANT DIFFERENCE, P=.05, P=.01 AND P=.001 SIGNIFICANT DIFFERENCE RESPECTIVELY.

\* HOMO-CYSTEINE THIOLACTONE NICOTINAMIDE

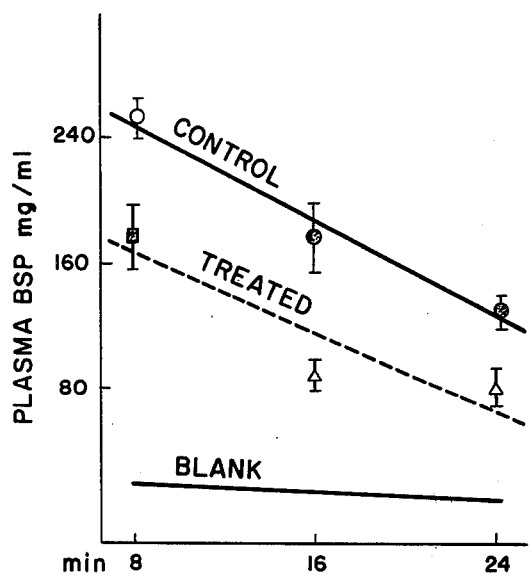
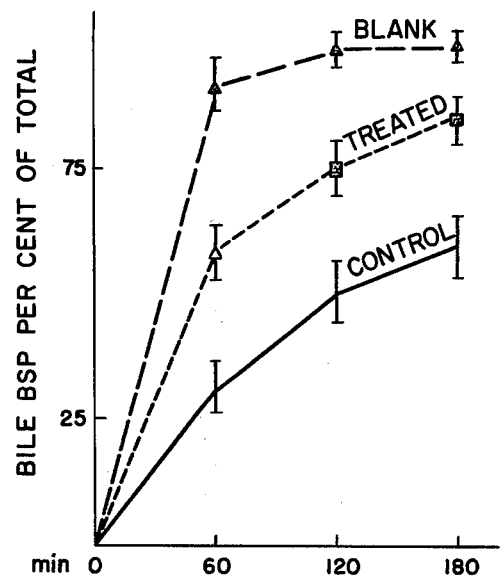

EFFECT OF $ST_{22}^{*}$ ON BSP CLEARANCE IN RATS ORALLY INTOXICATED WITH $CCl_4$

FIG. 2: PLASMA BSP CLEARANCE IN RATS TREATED WITH 250 MG/KG OS 1-HOUR BEFORE, 7 AND 23 HOURS AFTER $CCl_4$ (5 PER GROUP).

FIG. 3: CUMULATIVE BILE EXCRETION OF BSP IN PER CENT OF TOTAL ADMINISTERED IN RATS TREATED WITH 50 MG/KG S.C. AT THE SAME TIMES AS ABOVE (15 PER GROUP). BSP ADMINISTERED 3 HOURS AFTER LAST DOSE OF $ST_{22}$. AVERAGE VALUES ±S.E.M. STUDENT'S "T" TEST VS CONTROLS. ▩, △ AND ▲ INDICATE A P=.05, P=.01, AND P=.001 SIGNIFICANT DIFFERENCE RESPECTIVELY.

* HOMO-CYSTEINE THIOLACTONE NICOTINAMIDE

DERIVATIVE OF NICOTINIC ACID WITH AMIDES

RELATED APPLICATIONS

This application is a Continuation-in-Part of patent application Ser. No. 451,694 filed Mar. 15, 1974 and herewith abandoned.

FIELD OF THE INVENTION

This invention relates to the novel homocysteine thiolactone of nicotinamide and its salts and more particularly to its synthesis, utility and modes for its useful administration.

THE INVENTION

The compound: homocysteine thiolactone of nicotinamide having the formula:

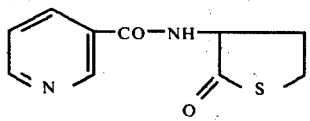

and its pharmacologically acceptable salts have useful pharmacological activity related to liver function and indicated therapeutic activity in lowering cholesterol, free fatty acid, and triglyceride, plasma levels and in improving BSP bile clearance in conditions where such effects are indicated.

DETAILED DESCRIPTION OF THE INVENTION

The invention above will be more fully described by the appended examples and by references to the drawing where:

FIG. 2 shows the effect of the compound of this invention on BSP handling in liver damaged rats.

FIG. 3 shows the effect of the compound of this invention upon the cumulative bile excretion of BSP in liver-damaged rats.

Figure 1:
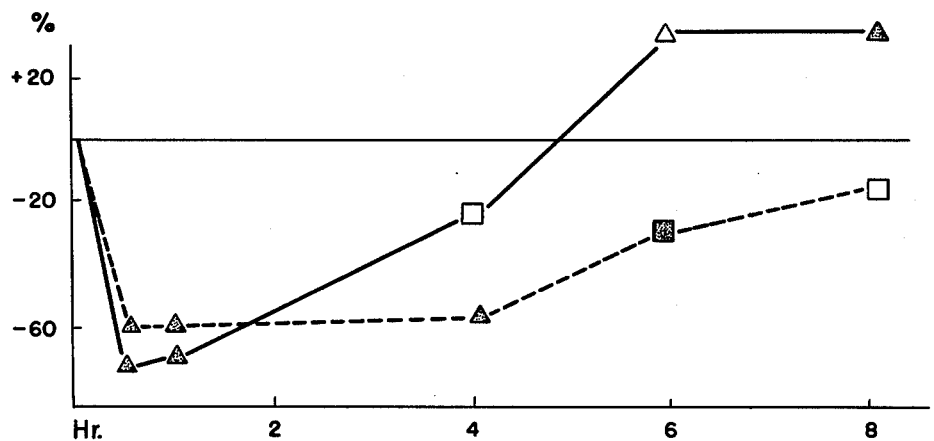
FIG. 1 shows the effect of the compound of the invention on lipid metabolism (FFA and triglycerides) in fasted rats.

The compound is prepared by reacting nicotinyl chloride hydrochloride or nicotinic acid esters with homocysteine thiolactone hydrochloride in an anhydrous organic solvent inert to the reactants. Preferably the reaction is carried out in the presence of halacid acceptors. Dioxane, tetrahydrofurance, (THF), N,N-dimethyl formamide (DMF). DMF is preferred. The solvent medium may include an anhydrous proton or haloacid acceptor. Among such anhydrous acceptors are triethylamine, other trialkylamines, pyridine etc. Triethylamine or pyridine are preferred.

The reaction proceeds at temperatures between 25° and 125° C. Preferably the reaction provides a purer product in best yield at temperatures in the range 90° ± 10° C.

The product is purified by recrystallization from ethyl acetate. The chromatographically pure produce melts in the range 150° – 152° C.

The compound, homo-cysteine thiolactone nicotinamide, may be prepared into non-toxic pharmaceutically acceptable salts with organic acids such as acetic, citric, tartaric, salicylic, maleic etc. or with inorganic acids such as hydrochloric and hydrobromic acid, sulfuric acid, nitric acid, and phosphoric acid.

This compound (and its salts) has been found to be active pharmacologically by reducing cholesterol, free-fatty acid and triglyceride levels in the plasma after administration. This pharamacological activity is associated with the function of the compounds in the liver and the compound has been noted to counteract abnormalities resulting from experimentally-induced liver malfunction, thus indicating therapeutic activity.

The exact mode or situ of such activity in the organism is as yet unclear but the activity is unmistakable. An additional factor of utility of the compounds for therapy is its low toxicity, high therapeutic index.

The appended examples indicate a useful simple and preferred synthesis of the novel compound, its pharmacological activity and its therapeutic activity. The synthetic methods and the modes of administration are merely exemplary. All art-recognized equivalent methods and materials are intended.

EXAMPLE 1

Homocysteine thiolactone of nicotinamide: (ST-22)

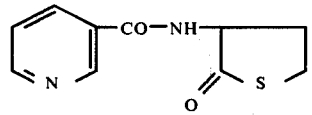

Suspend 1 mole of nicotinic acid chloride hydrochloride in N-N-dimethylformamide; slowly and under stirring add 3.3 moles of anhydrous triethylamine and homocysteine thiolactone hydrochloride previously dissolved in N-N-dimethylformamide. The reaction vessel is equipped with a stirrer and a reflux condenser. The reaction mixture is maintained for 4 hours at 90° C with stirring. The reaction product is filtered. The N-N-dimethylformamide solution is evaporated to dryness and then the residue is recrystallized from ethyl acetate.

The melting point of the chromatographically pure product obtained is 150° – 152° C.

EXAMPLE 2

The compound of Example 1 (ST-22) has an $LD_{50}$ of 4500 mgm/kg per os and 2400 mgm/kg e.p. in rats.

EXAMPLE 3

Pharmacological Activity

The pharmacological activity of the compound ST-22 was assessed by using the methods described in the following articles.

A—The antilipolytic activity in the fasting state was studied in accordance with 1. Carlson L. A. and E. R. Nye, Acute Effect of Nicotinic Acid In the Rat. Plasma and liver lipids and blood glucose. Acta. Med. Scand., 179, 453, 1966.

2. Dalton C., C. Van Trabert and J. X. Dwyer, Relationship of Nicotinamide and Nicotinic acid to Hypolipidemia, Biochemical Pharmacology, 19, 2609, 1970.

3. Bizzi A. and S. Garattini, Drugs Lowering Plasma Free Fatty Acids: Similarities and Dissimilarities with the Nicotinic acid Effect, p. 207; K. F. Gey and L. A. Carlson Edrs., Hans Huber Publisher, Bern Stuttgard Vienna, 1971.

B — The antilipolytic activity in the case of Nor-Adrenaline stimulated lipolysis in rats was investigated in accordance with 1. S. Garattini and A. Bizzi, Inhibiteurs de la mobilization des acides gras libres, Actualite Pharmacologiques XXII Serie, 169, 1969.

C — The hypolipidaemic activity was studied in accordance with

1. Assous E., Pouget M., Nadand J. ecc., Etude d'un novel hypolipidemiant — le bis (hydroxy-ethyl-thio) 1-10 decane, Therapie, 27, 395, 1972.

D — The activity in experimental liver injury was studied according to

1. Schwarzmann W., Les hepatites toxiques experimentales, Revue Int. d'Hepatol., 5, 387, 1957.
2. Stern P. H., T. Fuzukuwa, T. M. Brody, Rat liver and plasma lipids after CC14 administration, J. Lipid Res., 6, 278, 1965.

The new compound of Example 1 (ST-22) exhibited the following pharmacological activity in the above detailed tests:

1. Antilipolytic action: threshold dose 39/mg/kg os. 156 mg/kg os reduced the plasma levels of F.F.A. by 70%, triglycerides by 60% in the 17-hour fasted rats (FIG. 1) and reduced the lipolytic activity of subcutaneously injected Nor-adrenaline by 75% in rats.
2. Hypolipidaemic action: 156 mg/kg os for 15 days had an inhibitory effect against the increase in plasma total lipids, cholesterol and $\beta$-lipoproteins induced by an atherogenic diet in rats.
3. Action on experimental liver injury: does of 156 mg/kg os or 78 mg/kg os or subcutaneously reduced changes in the biochemical pattern (plasma GPT, GOT, LDH, total lipids, triglycerides, cholesterol and glycogen) induced by carbontetrachloride intoxication, and increased plasma clearance and biliary-excretion of Bromsulphonphtalein (FIGS. 2 and 3).

The high therapeutic index of the compound was noted. (ST-22) homo-cysteine thiolactone nicotinamide clearly reduces hyperlipidaemic levels resulting from stimulated lipod mobilization and liver injury induced by chlorinated hydrocarbons and is useful in therapy where such activity is indicated as in altered, lipid metabolism rates or liver injury.

EXAMPLE 4

The various experimental animals used in the above tests were carefully observed and no untoward or unusual toxic syndromes were noted in other than the $LD_{50}$ test. It was noted however, that ST-22 demonstrated a slow-acting hypotensive effect which differed from the rapid vaso-dilation hypotensive effects noted with nicotinic acid.

The invention includes within its scope pharmaceutical preparations containing, as an active ingredient, the therapeutically active compound (ST-22) homocysteine thiolactone nicotinamide or the non-toxic acid addition salts thereof, in association with a pharmacologically acceptable carrier. Other therapeutic and compatible materials may be included in the preparation. The preparations may take any of the forms customarily employed for administration of therapeutically active substances, but the preferred types are those suitable for oral administration and especially tablets, pills and capsules including the substance. The tablets and pills may be formulated in the usual manner with one or more pharmacologically acceptable diluents or excipients, for example lactose or starch, and include materials of a lubricating nature, for example calcium stearate. Capsules made of absorbable material, such as gelatin, may contain the active substance alone or in admixture with a solid or liquid diluent. Liquid preparations may be in the form of suspensions, emulsions, syrups or elixirs of the active substance in water or other liquid media commonly used for making orally acceptable pharmaceutical formulations, such as liquid paraffin, or a syrup or elixir base. The active substance may also be provided when indicated, in a form suitable for parenteral administration, i.e.e as a solution suspension or emulsion in sterile water or an organic liquid usually employed for injectable preparations, for example a vegetable oil such as olive oil, or a sterile solution in an organic solvent.

The following Examples illustrates the preparation of a pharmaceutical composition according to the invention.

EXAMPLE 5

25 g of ST-22

25 g of Avicel PH 101 (microcrystalline cellulose) and 25 g of Aerosil (highly purified silicon dioxide) are mixed together and gelatin capsules are filled each with the mixture so that each capsule contains 10 mg of active substance ST-22.

EXAMPLE 6

800 g of lactose and 200 g of maize starch are mixed with 200 ml of 5% maize starch in water. The mixture is granulated, dried at 55° C and sieved through a no. IV sieve (Sieve opening 0.7 mm).

1000 g of the granulate are mixed with 100 g of ST-22 and gelatin capsules are filled each with the mixture so that each capsule contains 10 mg of the active substance ST-22.

What is claimed:

1. The compound homocysteine thiolactone nicotinamide:

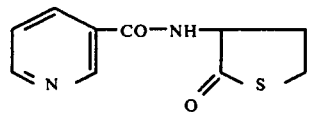

and the non-toxic, pharmacologically acceptable salts thereof.

* * * * *